Figure 1:
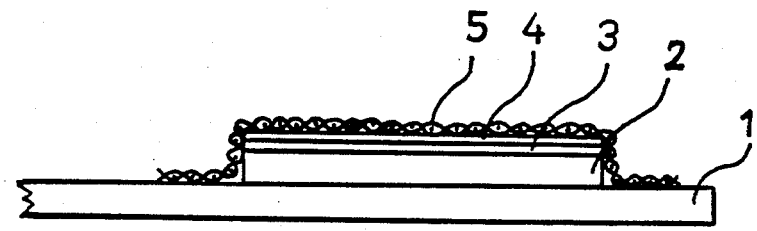

United States Patent [19]

Rothe et al.

[11] Patent Number: 4,587,099
[45] Date of Patent: May 6, 1986

[54] TEST STRIPS FOR THE DETECTION OF A LIQUID SAMPLE COMPONENT

[75] Inventors: Anselm Rothe; Adolf K. Selle, both of Birkenau; Bernward Sojka, Viernheim, all of Fed. Rep. of Germany

[73] Assignee: Boehringer Mannheim GmbH, Mannheim, Fed. Rep. of Germany

[21] Appl. No.: 677,899

[22] Filed: Dec. 5, 1984

Related U.S. Application Data

[63] Continuation of Ser. No. 372,416, Apr. 27, 1982, abandoned.

[30] Foreign Application Priority Data

May 9, 1981 [DE] Fed. Rep. of Germany ....... 3118381

[51] Int. Cl.[4] .................... G01N 21/78; G01N 33/52
[52] U.S. Cl. .......................................... 422/56; 422/58
[58] Field of Search ................. 422/55, 56, 57, 58, 422/66

[56] References Cited

U.S. PATENT DOCUMENTS

| | | | |
|---|---|---|---|
| 3,526,480 | 9/1970 | Findl et al. | 422/66 |
| 3,555,129 | 1/1971 | Fukada et al. | 264/41 |
| 3,585,004 | 6/1971 | Mast | 422/56 |
| 3,630,957 | 12/1971 | Rey et al. | |
| 3,802,842 | 4/1974 | Lange et al. | 422/57 X |
| 3,992,158 | 11/1976 | Przybylowycz et al. | |
| 4,050,898 | 9/1977 | Goffe et al. | |
| 4,066,403 | 1/1978 | Bruschi | |
| 4,160,008 | 7/1979 | Fenocketti et al. | 422/56 |
| 4,211,845 | 7/1980 | Genshaw et al. | 435/14 |
| 4,299,917 | 11/1981 | Berger et al. | 435/19 |

FOREIGN PATENT DOCUMENTS 2940165 11/1980 Fed. Rep. of Germany .

*Primary Examiner*—Arnold Turk
*Attorney, Agent, or Firm*—Felfe & Lynch

[57] ABSTRACT

A test strip for analyzing a liquid sample has a carrier or handle, a slowly-absorbent layer fixed thereupon which slowly sucks up the liquid sample, a liquid impermeable layer fixer thereover, an absorbent reagent layer fixed thereover, and a mesh covering these, which mesh layer is fixed next to the slowly-absorbent layer on to the carrier. The mesh and layer portions of the test strip can thus be briefly immersed in the liquid sample with the carrier and withdrawn for observing the analyzing reaction of the reagent and liquid sample absorbed into the absorbent reagent layer through the mesh, the mesh serving to conduct excess liquid sample from the adjacent surface of the absorbent reagent layer to the still absorbent slowly-absorbent layer so that the excess liquid sample does not interfere with the observation of the reaction.

10 Claims, 1 Drawing Figure

TEST STRIPS FOR THE DETECTION OF A LIQUID SAMPLE COMPONENT;

This application is a continuation of application Ser. No. 372,416, filed Apr. 27, 1982 and abandoned herewith.

This invention relates to test straps for the detection of a component in liquid samples, especially in a body fluid.

Test strips have already been in use for a long time, but recently they have achieved increasing importance, especially in clinical chemistry. One or more test zones, which for economic reasons are relatively small, on each strip are fixed onto a water-resistant handle, normally a synthetic resin rodlet. The test strips permit a rapid, simple, semi-quantitative or quantitative determination of the components of a liquid sample, for example of glucose, protein and the like in body fluids, such as urine, serum and the like. To an increasing extent, such test strips are also used by lay persons so that it has become necessary to simplify the handling thereof as much as possible and also to make them more reliable in use.

An extraordinarily frequent mistake in using such test strips is the non-uniform moistening of the test strip with the sample due to an insufficient wiping off of excess sample after dipping the test strip into the sample. Droplets of liquid remaining behind on the test zone lead to a non-informative test-result coloration because either too high a substrate informative concentration is simulated by the residual liquid, or the entry of atmospheric oxygen which is sometimes required as a reaction component, for example for all enzymatic oxidation reactions, is prevented, so that too low a substrate concentration is simulated. Furthermore, residual liquid which, in the case of multiple tests, forms a liquid bridge between the different test zones, leads to a transmission of reagents from one test zone to another, so that, especially in the peripheral regions of the test zones, disturbing reactions can result which make reading the test difficult or impossible.

Consequently, Federal Republic of Germany Patent Specification No. 21 18 455 suggests underlaying the test zones on a water-resistant handle, with an absorbent material or paper which suck up an excess of test liquid which remains behind after briefly dipping the test strip into the test liquid and wiping it off. If the absorbent material is a hydrophobed paper, however, it sucks up, via its less hydrophobed cut edges, any possible liquid bridges to neighboring zones relatively quickly and, in addition, is able to suck up an excess of liquid from the test paper without, however, removing the liquid necessary for the reaction.

Furthermore, Federal Republic of Germany Patent Specification No. 28 54 342 describes test strips in which an adsorbent paper (the absorbency of which may, however, substantially correspond to that hereinafter described as slow adsorbency) is separated from the reagent zone by a liquid-impermeable layer so that only liquid bridges between neighbouring test zones are sucked up, but the amount of liquid present in and on the test zone is not influenced, as was to have been expected and as verified by constructions of the device. Droplets or films of liquid thus remained on the test zone and led to non-uniform reaction and coloration.

In both of the above-mentioned Patent Specifications, paper is preferably used as the carrier material for the reagent (test) zone which has a relatively high water take-up ability so that small variations in the amount of test liquid can be tolerated.

Recently, thin polymer films in which the reagents are embedded have been increasingly used as the reagent carriers. In comparison with paper or other fibrous carrier materials, these possess a substantially more homogeneous structure and thus display a substantially more uniform coloration. They also have a more uniform surface so that the increasingly used photometric evaluations of a coloration can be carried out with correspondingly small remission photometers. Films of this kind are described, for example in Federal Republic of Germany Patent Specifications Nos. 15 98 153 and 23 32 760. In the first, the amount of liquid is regulated in that an excess of liquid is applied, allowed to penetrate into the thin polymer film for a definite period of time and the excess, together with possible turbidities which do not penetrate into the film, then are washed or wiped off. The observation of the coloration can then take place from above in the usual manner. In the second Patent Specification, the problem is solved in that the liquid is first sucked up into a hydrophilic layer and is transmitted from this more slowly in an amount corresponding to the absorbency of the actual reagent layers. In the case of this device, observation is made from the rear side, radiation-impermeable layers and filter layers between the reagent layer and the hydrophilic layer reservoir thereby ensuring that only the reaction product is evaluated in the reagent layer. Although such multi-layer devices can compensate for small dosage variations, such a device must not be dipped into the test liquid since the amount thereby applied would be "drowned". Thus, the two devices have, in comparison with the normal test strips using paper, an additional "dosaging step", which makes their use more complicated.

Thus, there is a problem in providing a test strip which can be simply handled.

As described above, with a device according to Federal Republic of Germany Patent Specification No. 28 43 342 in which a reagent film is fixed on to a water-impermeable thin carrier film, droplets or films of liquid remained on the test zone and here led to a non-uniform reaction and coloration. Surprisingly, however, we have now found that the liquid film present on the upper side of the test film can be sucked up quickly and reproducibly by the underlying hydrophobic paper when, over the test zone and the hydrophobic paper, there is stretched a thin mesh which is fixed to the handle on both sides of the test zone. Apparently due to capillary forces which are effective between the filaments of the mesh and the film surface, the excess liquid is rapidly and dependably conducted over the edge and sucked up by the hydrophobic paper.

Thus, according to the present invention, there is provided a multi-layer test agent for the detection of a component of a liquid sample, comprising a carrier, a slowly-absorbent layer fixed thereon which slowly sucks up the liquid sample, an absorbent reagent layer fixed thereabove, and a mesh layer covering these which mesh layer is fixed, next to the slowly absorbent layer, on to the carrier. The reagent layer consists of a polymeric film layer in which the reagents are embedded and is liquid-impermeably separated from the slowly adsorbent layer.

The construction of the test agent according to the present invention is illustrated by way of example in FIG. 1 of the accompanying drawing. This Figure shows a carrier element 1 on which are fixed an adsorbent layer 2, a water-insoluble film 3 and a reagent film 4, the latter two (3 and 4), for reasons of clarity of illustration, being shown thicker than the actually are, and a covering mesh 5.

The carrier 1 normally used can be a commercially available synthetic resin foil, but a water-resistant cardboard, a metal strip or the like can also be used in the same manner. However, it is important that the carrier 1 possesses sufficient strength to permit handling, is insert to the test (sample) liquid and the reagents employed, and permits simple fixing of the covering mesh layer 5.

The slowly absorbent layer 2 is preferably a somewhat hydrophobed paper but other absorbent materials can also be used, such as open-pored synthetic resin foams, blush polymers, liquid resistant gels and the like. Inorganic materials, for example gypsum, are less preferred since they normally do not possess a sufficient stability. The slow absorbency of these materials should be such that, upon briefly dipping into a liquid sample (1 to 2 seconds), they are only externally moistened but liquid bridges between multiple test zones (not shown), as well as excess sample on each test zone, are sucked up within 2 to 10 seconds, a normal reaction time for the test of 1 to 2 minutes being taken as the norm. If the test time is substantially longer, the absorbency time in which ideal conditions still do not prevail on the test zone, can, of course, be correspondingly prolonged.

The test films used can be indicator foils produced from synthetic resin dispersions according to Federal Republic of Germany Patent Specification No. 15 98 153, "open" indicator foils according to Federal Republic of Germany Patent Specification No. 29 10 134, blush polymers according to U.S. Pat. No. 3,555,129 and other thin, macroscopically homogeneous layers which take up the liquid sample to a limited extent. Since such thin layers are normally not sufficiently stable, so that they, together with the other components, can be used to construct the test agent, it is recommended to afix these films on to a stable, thin, pliable adjuvant foil, which normally consists of a solid synthetic resin, or to produce them directly thereupon and to work up the two together. However, since aqueous liquids normally only penetrate very slowly into such polymeric films, it is, however, also possible to produce the film in a thicker layer so that, on the one hand, it is sufficiently stable in order to be able to omit a carrier foil and, on the other hand, a passage through of the liquid within the time necessary for the test reaction to the slowly absorbent layer is prevented by the film itself, i.e. the polymeric film reagent layer assumes the additional function of the otherwise discrete impermeable layer.

The mesh layers used can be the covering meshes already described in Federal Republic of Germany Patent Specification No. 21 18 455, which can usually consist of synthetic resins, such as polyamides, polyesters or also cellulose derivatives. For optical transparency, it is recommended to use a relatively thin mesh with a filament thickness of 20 to 200$\mu$ and an open hole surface area of 40 to 80%. The filament material must, of course, be permeable to the radiation used for the analysis of the reaction product since evaluation takes place from above.

The following Examples are given for the purpose of illustrating the present invention:

EXAMPLE 1

Preparation of a glucose-sensitive test film

20 KU glucose oxidase
80 KU peroxidase
5 ml. 1M citrate buffer (pH 5)
0.13 g. sodium alginate
13 g. polyvinyl propionate dispersion (50%)
0.375 g. 3,3',5,5'-tetramethylbenzidine
0.1 g. 1-phenylsemicarbazide
1 g. dioctyl sodium sulphosuccinate
5 ml. methoxyethanol
10 g. silica gel
12 ml. water are worked up to give a homogeneous mass and coated with a 0.1 mm. gap width on to a 100$\mu$ thick polycarbonate foil. The foil thus obtained is cut up into 6 mm. wide strips which are stuck with a double-sided adhesive band in the region of one of the longitudinal edges of a 6 cm. wide strip of an approximately 0.5 mm. thick polyvinyl chloride foil. This is then cut up into 6 mm. wide pieces, transversely to the stuck-on strips.

When the test strips so obtained are briefly dipped into glucose-containing urine, then, after a reaction time of 1 minute, there are obtained green to blue colorations, gradiated according to the glucose concentration. In spite of careful wiping off of the test strips on the edge of the sample vessel, the test zone is non-uniformly coloured due to the non-uniform thickness of the liquid film remaining behind, whereby, due to the prevention of the admission of air to the places on which there is present a comparatively thick film of liquid, the reaction is weaker. After a reaction time of 5 minutes, in which the liquid film has dried completely, these places, due to the higher substrate concentration, appear, on the other hand, to be more strongly coloured.

A uniform coloration can be achieved when the test strips are dipped for about 30 to 60 seconds into the sample solution, after removal carefully dried by wiping with a soft wadding and the reaction read off after one minute.

EXAMPLE 2

Production of a hydrophobed layer

Filter paper (Schleicher & Schull 23 SL) is impregnated with the following solution and dried at 130° C.:
  50 ml. silicone resin HK 15a (Wacker)
  5 ml. hardener (10% aluminium acetylacetonate in toluene)
  1 liter n-butyl acetate The hydrophobed paper thus obtained is, analogously to Example 1, cut up into 6 mm. wide strips and stuck on to a polyvinyl chloride foil. By means of a further adhesive band, an indicator foil according to Example 1 is fixed on to the hydrophobed paper and again cut up transversely to these bands into 6 mm. wide strips.

When strips thus obtained are briefly dipped into glucose-containing urine, it can be observed that a urine bridge next to the test zone is rapidly sucked up by the hydrophobed paper and removed, whereas a possibly non-uniform liquid film remains behind on the test film as in Example 1 and slowly dries. The reaction with various glucose concentrations and the non-uniform coloration correspond completely with the observations in Example 1.

EXAMPLE 3

Production of a glucose test according to the invention

A polyvinyl chloride foil according to Example 1 is coated on one side with a melt adhesive upon which are placed, on top of one another, a hydrophobed paper strip according to Example 1, a glucose test film strip according to Example 1 and an approximately 12 mm. wide nylon mesh (filament thickness 60μ, 45% open hole surface area). With the use of a heated roller which, at the position of the test film, has a 2 mm. deep recess, the nylon mesh is pressed into the melt adhesive and thus fixed on to both sides of the test film. Thereafter, again as in Examples 1 and 2, 6 mm. wide strips are cut off. The test film and the hydrophobed paper are rigidly held in the pocket formed between the nylon mesh and the carrier foil but they can, nevertheless, be pulled out with some difficulty by means of tweezers.

The result is a test strip for analyzing a liquid sample from a reaction thereto in the test strip. The test strip comprises a liquid-impermeable carrier, whereby the test strip may be handled; a hydrophobed filter paper layer having edges extending between opposite sides of the layer, one of the sides facing the carrier; a liquid-impermeable layer for impermeability to the liquid sample on the side of the hydrophobed filter paper layer opposite that facing the carrier; an adsorbent reagent layer having a reagent which produces the reaction to the liquid sample from which the liquid sample is analyzed when the liquid sample is adsorbed therein adhered to the side of the liquid-impermeable layer opposite that adhered to the hydrophobed filter paper for absorbing the liquid sample; and a mesh adhered to the carrier sufficiently close to at least two of the edges of the hydrophobed filter paper layer for fluid communication therewith and extending over the layers for holding the layers in the pocket thereby formed between the mesh and the carrier. The hydrophobed filter paper layer comprises a filter paper impregnated with a dried solution of silicone resin, a hardener comprising about 10% aluminum acetylacetonate in toluene and n-butyl acetate in the solution volume proportions of about 0.05, 0.005, and 1, respectively, whereby the filter paper is hydrophobed. The mesh commmprises nylon filaments of about 60μ thickness, the mesh having an open hole surface area of about 45%. Finally, the mesh and layers together have a thickness from the liquid-impermeable carrier of about 2 mm.

When the test strip thus obtained is dipped for about one second into urine and then wiped off gently on the edge of the sample vessel, it is then possible to ascertain that the liquid bridges present next to the test zone are quickly sucked up and the surface of the device, which is initially shiny due to the liquid film present between the mesh holes, becomes matt after 2 to 5 seconds, which means that excess liquid also on the test surface is sucked up by the hydrophobed paper. In contradistinction to the test devices according to Examples 1 and 2, the total surface of the test film is, depending upon the glucose concentration, more or less strongly but uniformly coloured.

It will be understood that the specification and examples are illustrative but not limitative of the present invention and that other embodiments within the spirit and scope of the invention will suggest themselves to those skilled in the art.

What is claimed is:

1. A multi-layered test strip for detecting a component of a liquid sample, comprising: a carrier; a slowly-absorbent layer on the carrier for slowly sucking up a liquid sample; reagent layer means comprising an absorbent reagent-containing layer on the slowly-absorbent layer opposite the carrier for absorbing sufficient of the liquid sample when dipped therein for the reagent contained therein to react with the liquid sample and detect thereby the component of the liquid sample; and a mesh conductive of the liquid sample, covering the layers, sufficiently contiguous to the slowly-absorbent layer for fluid communication therewith, and fixed to the carrier, the absorbent reagent-containing layer comprising a absorbent polymeric film layer in which the reagent is embedded and means for liquid-impermeably preventing passage of the liquid sample therethrough to the slowly-absorbent layer.

2. A test strip for analyzing a liquid sample for a reaction thereto in the test strip, the test strip comprising:
   a carrier, whereby the test strip may be handled;
   a slowly-absorbent layer having a slow absorbency to a liquid sample on a portion of the carrier;
   a liquid-impermeable means impermeable to the liquid sample on the side of the slowly-absorbent layer opposite the carrier for aiding the slow absorbency of the slowly-absorbent layer;
   an absorbent reagent-containing layer on the side of the liquid impermeable means opposite the slowly-absorbent layer, the absorbent reagent-containing layer having an absorbency to the liquid sample and a reagent which produces the reaction with the liquid sample when absorbed therein from which the liquid sample is analyzed; and
   a mesh substantially covering the side of the absorbent reagent layer opposite the liquid impermeable means, being conductive of the liquid sample, and extending sufficiently next to the slowly-absorbent layer for establishing communication of the liquid sample from the mesh to the slowly-absorbent layer,
   the slow absorbency of the slowly-absorbent layer being sufficiently slow relative to the absorbency of the absorbent reagent-containing layer that the layers may be immersed in the sample liquid for a time sufficient to absorb into the absorbent reagent-containing layer sufficient liquid sample for the reaction therein and thereafter still having absorbency to the liquid sample and sufficiently fast, in combination with the liquid-sample conductiveness of the mesh and communication of the liquid sample from the mesh to the slowly-absorbent layer, to absorb sufficient liquid sample from the mesh side of the absorbent reagent-containing layer after it is removed from immersion in the liquid sample as would interfere with the analysis of the liquid sample from the reaction in the absorbent reagent-containing layer.

3. The test strip as claimed in claim 2, wherein the slowly-absorbent layer is hydrophobed paper.

4. The test strip as claimed in claim 2, wherein the carrier is impermeable to the liquid sample and the slowly-absorbent layer is fixed onto the carrier.

5. A test strip as claimed in claim 2, wherein the portion of the mesh next to the slowly-absorbent layer is fixed onto the carrier.

6. The test strip as claimed in claim 2, wherein the mesh is an optically transparent material whereby an optically-apparent analysis reaction in the absorbent reagent-containing layer can be observed through the mesh.

7. The test strip as claimed in claim 6, wherein the optically transparent material is a synthetic resin.

8. A test strip as claimed in claim 6, wherein the mesh comprises filaments from about 20 to about 200μ thickness and the mesh has an open hole surface area of from about 40% to about 80%.

9. A test strip for analyzing a liquid sample from a reaction thereto in the test strip, the test strip comprising:
   a liquid-impermeable carrier, whereby the test strip may be handled;
   a hydrophobed filter paper layer having edges extending between opposite sides of the layer, one of the sides facing the carrier;
   liquid-impermeable means impermeable to a liquid sample adhered to the side of the hydrophobed filter paper layer opposite that facing the carrier;
   an absorbent reagent-containing layer means having a reagent which produces a reaction to the liquid sample from which the liquid sample is analyzed when the liquid sample is absorbed therein adhered to the side of the liquid-impermeable means opposite that adhered to the hydrophobed filter paper for absorbing the liquid sample; and
   a mesh adhered to the carrier sufficiently close to at least two of the edges of the hydrophobed filter paper layer for establishing communication of liquid sample on the mesh to the hydrophobed filter paper and extending over the layers for holding the layers in the pocket thereby formed between the mesh and the carrier.

10. The test strip as claimed in claim 9, wherein:
    the hydrophobed filter paper layer comprises a filter paper impregnated with a dried solution of silicone resin, a hardener comprising about 10% aluminum acetylacetonate in toluene, and n-butyl acetate in the solution volume proportions of about 0.05, 0.005, and 1, respectively, whereby the filter paper is hydrophobed; and
    the mesh comprises nylon filaments of about 60μ thickness, the mesh having an open hole surface area of about 45%,
    the mesh and layers having a thickness from the liquid-impermeable carrier of about 2 mm.

* * * * *

UNITED STATES PATENT AND TRADEMARK OFFICE
CERTIFICATE OF CORRECTION

PATENT NO. : 4,587,099

DATED : May 6, 1986

INVENTOR(S) : Anselm Rothe et al.

It is certified that error appears in the above-identified patent and that said Letters Patent is hereby corrected as shown below:

```
Col. 1, line  2, delete ";" after title;
        line  8, "straps" should read -- strips --;
        line 57, "adsorbent" should read -- absorbent --
Col. 2, line 19, delete "are";
        line 26, delete "the case of"
        line 42, "28 43 342" should read -- 28 54 342 --
        line 62, delete "mesh layer"
Col. 3, line  2, "adsorbent" should read -- absorbent --
        line  5, "than the" should read -- than they --
Col. 5, line 28, "adsorbent" should read -- absorbent --
        line 45, "commprises" should read -- comprises --
Col. 6, line 13, "a" should read -- an --
Col. 7, line  7, "20" should read -- 20µ --
```

Signed and Sealed this

Twenty-fourth Day of March, 1987

Attest:

DONALD J. QUIGG

Attesting Officer

Commissioner of Patents and Trademarks